United States Patent [19]

Noble et al.

[11] Patent Number: 4,881,536
[45] Date of Patent: Nov. 21, 1989

[54] METHOD AND APPARATUS FOR PROSTHESIS PLACEMENT

[76] Inventors: Phillip C. Noble, 2601 S. Braeswood, Apt. 103, Houston, Tex. 77025; Hugh S. Tullos, 2151 Troon, Houston, Tex. 77019

[21] Appl. No.: 6,563
[22] Filed: Jan. 22, 1987
[51] Int. Cl.⁴ ............................................. A61F 1/04
[52] U.S. Cl. ........................................ 606/94; 623/22
[58] Field of Search ........ 128/92 VP, 92 VQ, 92 VV

[56] References Cited

U.S. PATENT DOCUMENTS

| | | | |
|---|---|---|---|
| 3,924,274 | 12/1975 | Heinke et al. | 128/92 VP |
| 4,274,163 | 6/1981 | Malcom et al. | 128/92 VQ |
| 4,365,357 | 12/1982 | Droenert | 128/92 VP |
| 4,462,394 | 7/1984 | Jacobs | 128/92 XP |
| 4,466,435 | 8/1984 | Murray | 128/92 VQ |
| 4,488,549 | 12/1984 | Lee et al. | 128/92 VP |
| 4,562,548 | 1/1986 | Kranz | 128/92 VP |
| 4,595,006 | 6/1986 | Burke et al. | 128/92 VQ |
| 4,650,489 | 3/1987 | Thompson | 128/92 VP |

*Primary Examiner*—C. Fred Rosenbaum
*Attorney, Agent, or Firm*—Dodge, Bush & Moseley

[57] ABSTRACT

An improved surgical procedure for orthopedic implantation of a prosthesis where the conventional metal prosthesis is provided with an integral collar of a bone cement compatible polymer coating of a desired thickness and shape. The collar thickness serves to operably effect a seal with the bone so the prosthesis becomes a pressurizing plunger during the last phase of inserting the prosthesis into the bone opening or cavity. A slowly developing pressure build up of the viscous bone cement provided by the tapered shape of the collar thickness assures bone cement flow into all bone crevices and minimizes bone cement porosity by reducing the size of the voids formed by entrapped air during curing of the bone cement. The preformed collar also provides a predetermined thickness or layer of bone cement at the critical structural locations in order to ensure the surgeon of optimum physical characteristics of the bone cement at that location and avoid direct contact of the metal prosthesis with the bone. The collar also functions as a positioning mechanism to assit the surgeon in proper positioning of the prosthesis. The precoated prosthesis is also disclosed and claimed.

7 Claims, 1 Drawing Sheet

FIG. 1
FIG. 3
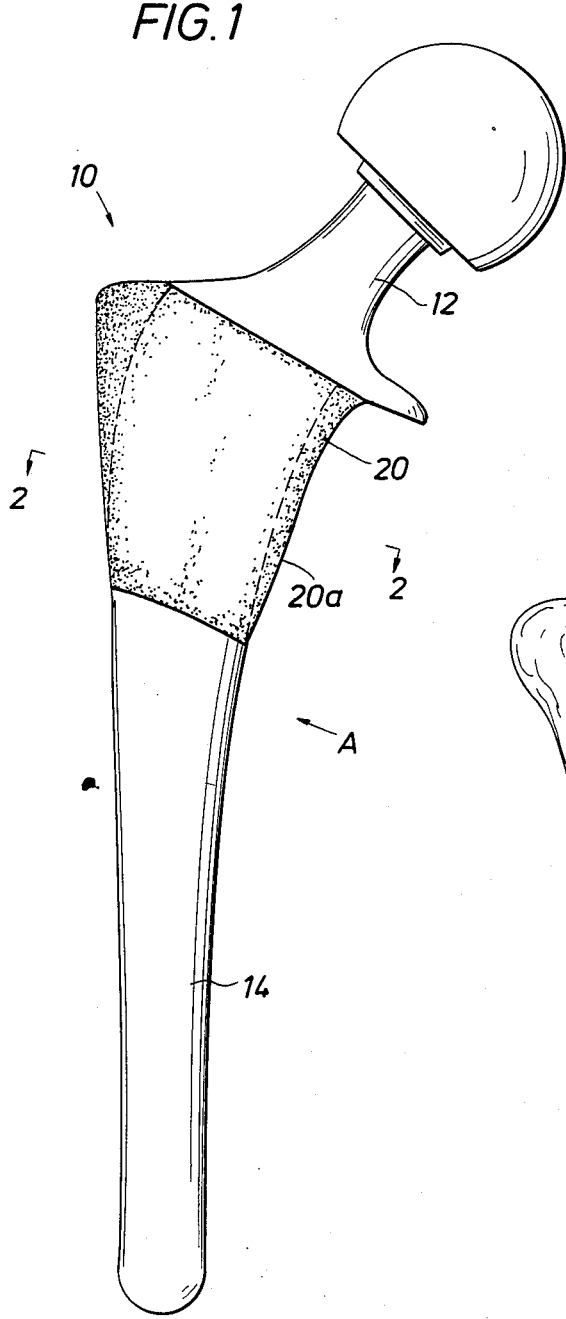
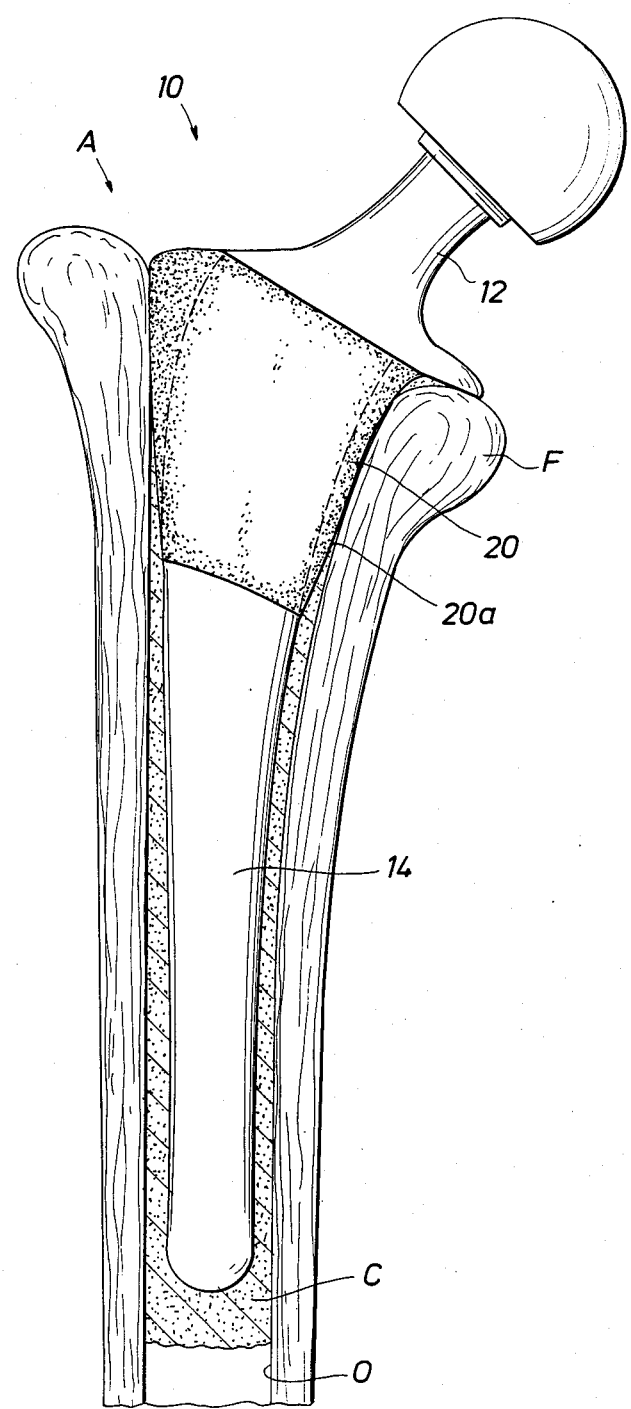
FIG. 2
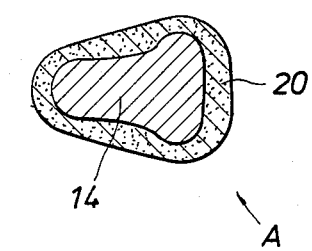

METHOD AND APPARATUS FOR PROSTHESIS PLACEMENT

BACKGROUND OF THE INVENTION

1. Field of the Invention

The present invention relates generally to the field of surgical replacement of a diseased or damaged bone joint of a warm blooded mammal and specifically to the fixation of a prosthesis device in a human.

2. Background Art

An improved process and apparatus for orthopedic implantation of a prosthesis in a warm blooded mammals disclosed by Park in U.S. Pat. No. 4,266,303 is entitled "Method of Orthopedic Implantation and Implant Product". This patent described at some detail implant techniques and developments, and is hereby specifically incorporated herein, along with each of the other specifically identified patents, as part of the written description of the present invention. The Park patent disclosed a metal implant prosthesis provided with a uniform thin polymer bone cement coating on substantially the entire stem or surface portion of the prosthesis that is to be affixed to the bone. The preformed acrylic polymer bone cement coating is cured or polymerized under controlled conditions of temperature, pressure and environment to achieve desired optimum mechanical properties prior to being implanted. The preformed polymeric coating is selected to be chemically compatible with the bone cement to be used during the surgical implant procedure to insure the effecting of a strong chemical bond therebetween and greatly enhance the structural connection of the prosthesis to the bone.

U.S. Pat. No. 4,012,796 to Weisman et al. discloses an "Interpositioning Collar for Prosthetic Bone Insert". The separate collar or flange is formed by a low modulus of elasticity material in order to reduce stress concentration at the critical neck location placed on the bone cement or bone by the much stronger metal prosthesis. Preferably, ultra high molecular weight polyethylene or similar materials are used to form the collar and which are not bonded to the stem. The bone cement contacting stem of the prosthesis is held firmly within the intramedullary canal of the bone by the collar and methyl methacrylete bone cement which is used as a grouting agent. The stresses ordinarily imposed upon the calcar and the medial wall of the bone at the highly stressed attachment point are minimized because of the impact and force absorptive characteristics of the low modulus of the elasticity of the plastic component used in the collar and which has the necessary rigidity combined with flexibility and resiliency to absorb shocks as well as stresses which are normally imposed upon the bone structure. Apparently, the separate collar, which may be circular or U-shaped is operably positioned during surgery and while the bone cement is still in the viscous stage.

A number of the recognized problems relating to the use of bone cement have been addressed in three patents to Raab. U.S. Pat. No. 4,281,420 propose to enhance the bone cement—prosthesis interface by treating the entire boundary layer or bone cement contacting surface of the prosthesis stem with a thin layer of bone cement cured under optimum conditions. The annealed and cured film interacts with the ambient cured bone cement used during the surgical implant technique to enhance the interface strength. The preferable film thickness is stated to be about 0.002 inch, but may be much less. The related Raab patents incorporated herein are U.S. Pat. Nos. 4,336,618 and 4,365,359, and the chapter entitled "Mechanical Properties of Bone Cements In Vitro and In Vivo" identified as a reference in U.S. Pat. No. 4,365,359, is also incorporated by reference herein.

The three Raab patents involved the use of a metal prosthesis having a polymer precoated stem portion which is inserted into the interior of the bone. The polymer precoat is or is compatible with bone cement which is stated to comprise a mixture of polymethyl methacrylate (commonly referred to as PMMA polymer and methyl methacrylate monomer) and optionally including a styrene co-polymer of PMMA. After the surgeon has formed the desired opening in the bone and the prosthesis is ready to be affixed, the bone cement is prepared in the operating room. Each batch of bone cement mixed has slightly different final characteristics due to the conditions under which that batch is prepared. The dough like mixed bone cement is placed in the opening by the surgeon and the prosthesis properly positioned relative to the bone by the surgeon. The bone cement is then allowed to cure in place. The PMMA cement is typically applied by the surgeon in a highly viscous doughy state with the potential for an inadequate degree of contact between the implant and the bone cement.

U.S. Pat. No. 4,302,855 to Swanson is entitled "Plug for the Intramedullary Canal of a Bone and Method". The disclosed bone plug is formed to control or restrict the flow of bone cement used to affix a prosthesis to a bone. The resilient plug body is configured or formed in a frusto-conical shape and is surgically inserted into the intramedullary canal a sufficient distance to avoid contact with the prosthesis stem while forming a flow plug in the canal. When the prothesis stem is being fixed to the human bone, the plug serves to block escape or passage of bone cement through the intramedullary canal from adjacent the prosthesis stem during both insertion and curing of the prosthesis. If the plug operates perfectly, and the surgeon has no way of verifying or correcting for improper plug operation during surgery, several desired goals are accomplished. First, by blocking the intramedullary canal, body fluid contamination or dilution of the bone cement during curing is reduced. The second purpose is to permit the bone cement to be worked in the canal under pressure where it be forced into the bone intertices to enhance mechanical strength and minimize voids in the bone cement formed by trapped air. Under pressure, the dough like consistency of the bone cement can thereby achieve a better mechanical configuration of fit to the bone structure and bond to the prosthesis.

U.S. Pat. No. 4,283,799 to Pratt, et al is entitled "Precoated Body Implant". The disclosed metal joint prosthesis is provided with a stem portion that attaches to or is inserted into a surgically formed opening in a skeletal member of a human body. The bone cement contacting surface portion of the stem is precoated with a layer (preferably three to five millimeters in thickness) to increase the strength of the prothesis—bone cement interface. Due to the substantial difference in the Young's or elastic modulus (stress vs. strain) of the hardened cement and the metal prosthesis such relative strength become critical and the gradual transition is highly desirable. The preformed coating also serves the purpose of spacing the prosthesis stem from the bone to avoid potentially damaging direct contact therebetween and assures an optimal minimum thickness.

Conventional engineering and processing procedures can be employed to produce a layer of prebonded cement with the desired mechanical properties and devoid of trapped air bubbles or other defects prior to the surgical procedures. By gradually tapering the elastic properties from the implant into the cement and on in fact to the surrounding bone produces a system which would have a minimal relative motion or strain between the different surfaces and would enhance the interface bonding.

Pratt further discloses that an optimum thickness precoating of a metal prosthesis insures there will be no direct prosthesis or metal to bone contact in the event of improper positioning. That is, the prosthesis will be assured at least some interface cement covering and the covering will be of optimal minimum essential thickness at the critical or high stress transfer points. Also, by increasing the mass of the prosthesis with the polymerized cement layer, better compaction of the doughy cement into the intertices of cancellous bones can be achieved. The larger stem tends to act as a plunger during insertion for forcing the doughy cement under pressure into the cancellous bone.

As mentioned previously, the bone cement is conventionally batch mixed in the operating room as required and each batch may vary from optimum strength. During preparation of the dough like mixture, substantial quantities of air are easily entrapped. Such entrapped air remains as a porosity in the cured cement mantle and greatly reduces its strength. By applying a pressure or exerting compressive forces on the cement the porosity may be substantially reduced through reduction of the total volume of pores and the size of the cement voids which remain.

At the time of the Pratt patent, only two bone cements were approved for surgical use by the Federal Drug Administration although any others should be considered within the scope of the present invention. The two approved compositions were both two component systems which are mixed and kneaded until a doughy consistency is obtained. Immediately after mixing, the doughy cement is forced into the bone cavity which has been surgically prepared to receive the prosthesis. The bone cement is forced into the cavity with adequate pressure to place the doughy mixture into the intertices of the bone to provide a good physical interlock by the bone cement after curing. Subsequent to placement of the doughy mixture within the cavity, the prosthesis is then inserted or properly located within the bone cavity. In the case of the prosthesis of Pratt, the precoated surface may be treated during surgery with a suitable monomer or chemical to make the surface tacky or dissolve some of the surface of the polymer precoat prior to insertion and thus foster a good interfacial bond between the preformed bone cement and the new bone cement.

SUMMARY OF THE INVENTION

The present invention relates to the field of a method and apparatus for orthopedic implantation of a prostheses utilizing bone cement as a fixative for the implant.

A conventional metal prosthesis is precoated with a polymer collar shaped so that as the stem portion is received in the opening of the bone the stem will also serve as a sealed plunger during the final increment of insertion or movement into the bone opening. The preformed collar of bone cement or bone cement compatible polymer material is also located at the anticipated high stress areas of contact with the bone. By preforming a collar of thickness equal to or greater than the minimum desirable value the surgeon is assured both of the strength of the cement mantle and proper thickness at the critical stress location.

An object of the present invention is to provide a new and improved method and apparatus for surgical replacement of bone joints.

A further object is to provide a new and improved method and apparatus for assuring an orthopedic surgeon of optimum bone cement strength and thickness during implant procedures.

Another object is to provide a new and improved method and apparatus for assuring a surgeon of proper bone cement porosity by pressurization of the bone cement during curing.

BRIEF DESCRIPTION OF THE DRAWINGS

FIG. 1 is a side view of a hip prosthesis preformed or modified in accordance with the present invention; and FIG. 2 is a view taken along line 2—2 of FIG. 1; and FIG. 3 is a view, in section, of a human femur having the modified hip prosthesis of FIG. 1 surgically installed.

DESCRIPTION OF THE PREFERRED EMBODIMENT

The present invention relates to an improvement in the orthopedic implantation of a joint prosthesis. While the surgical techniques and procedures described herein will be described in the context of a implantation of a hip prothesis, it will be understood by one skilled in the art that the method and apparatus disclosed herein are suitable for use in similar implant techniques for any bone joint involving both humans and animals and the present invention should not be considered limited to any particular bone implantation of a human.

The contents of the prior art patents have previously been incorporated herein by reference, along with the article entitled "Mechanical Properties of Bone Cements in Vitro and in Vivo". This article, also previously incorporated by reference, recognizes the significant reduction in mechanical properties of bone cement resulting from porosity due to entrapped air and suggest the advantages of curing some of the bone cement under pressure (in vitro) prior to surgery. However, none of the known prior art suggests addressing the problem of maintaining under pressure the bone cement when curing in the patient during surgery (in vivo). The present invention accomplished that new operation or function for the surgeon during implant surgery.

In FIGS. 1 and 2, the apparatus A of the present invention is illustrated in the preformed condition. The apparatus A includes a conventional metal hip prosthesis 10 having a ball or joint forming extension portion 12 intended to operably connect with a hip socket (not illustrated) and a stem portion 14. The prosthesis 10 is formed using known material and techniques and may be selected from those commercially available from a number of suppliers. Conventionally, the prosthesis 10 is constructed of metal alloys such as stainless steel, titanium and cobalt-chromium alloys. Such known prosthesis 10 may vary from that illustrated in having a detachable ball on the ball forming portion 12 for providing a predetermined range of movement for a femur F (FIG. 3). Likewise, the stem portion 14 may have a different cross-section than that illustrated in FIG. 2 without departing from the scope of the present invention.

The metal implant 10 is modified in accordance with the present invention to the condition illustrated in FIG. 1. Rather than the thin uniform polymer coating on the entire stem 14, the present invention contemplates the formation of a tapered sleeve or ring like collar 20 on the prosthesis adjacent the last portion of the stem 14 to be inserted in the opening 0.

The prosthesis 10 to be implanted has the bonded coating or sleeve formed from collar 20 of any suitable polymeric material that is compatible with the bone cement to be employed during the implantation. Preferably, the preformed polymer collar is prepared from bone cement of the same or a compatible composition or that is to be used during the operative implantation procedure. The preformed collar is preferably bonded, cured or substantially completely polymerized under the optimum temperature and pressure conditions to produce a strong bond with the prosthesis and to provide optimum mechanical properties to the bone cement collar.

The manufacturing techniques used to form the integral collar 16 of the present invention are disclosed in the previously mentioned patents. The precoating of the prosthesis can be accomplished in accordance with the techniques disclosed in the previously mentioned Park U.S. Pat. No. 4,266,303.

FIG. 3 illustrates the apparatus A when surgically installed or implanted in a patient's femur F or other suitable bone. The femur F has an intramedullary canal forming an opening 0 for receiving the stem portion 14 of the prosthesis 10 and which is secured therein by suitable bone cement C cured in vivo or in vitro. The opening 0 in the bone F is prepared by the surgeon using conventional techniques and should not be considered as limiting on the present invention. These aspects will be properly considered in anticipation of the specific implant and at which time the surgeon will be able to select the optimum approach. For purposes of the present invention, the significant aspects are development of the desired spacing of the metal stem 14 from the femur F and the dimensions of the opening 0 that will be sealingly engaged by the prosthesis collar 20 during the final increment of insertion into the openings.

The actual shape of the collar 20 will be dictated by the surgeon's requirements for each implant. The annular thickness of the collar 20 does need to be uniform, but rather only of sufficient thickness to operably seal with the bone F adjacent the opening 0 during insertion into the opening 0. Actual physical contact of the collar 20 with the bone F may not be necessary as the viscous nature of the bone cement C may enable desired bone cement pressurization during implantation and curing.

Preferably, the collar 20 is tapered at surface 20a in the manner illustrated to apply a controlled gradual rise in pressure of the bone cement C during the last increment of movement of the prosthesis 10 into the opening 0. The initiation of the pressure build up by collar 20 is controlled by the length of the collar 20 formed on the stem 14. This gradual increase in cement pressure enables or provides time for the bone cement C to collapse entrained air pockets and fully conform to the bone F and stem 14. The taper of surface 20a, may be modified or eliminated entirely if desired. Due to the pressure created on the bone cement it is not believed necessary to precoat the entire stem portion 14 of the prosthesis 10, but that option is available.

A significant aspect of the present invention is the thickness of the annular collar 14 to applied during the preforming on the prosthesis. This will, in significant part, be controlled or dictated by a number of factors such as the particular anticipated level of mechanical forces to be transmitted at the critical location of the collar. The major factor will be the size and shape of the bone opening 0 to be formed by the surgeon and to which the collar 20 must seal.

The preformed collar is also bonded to the surface of the prosthetic component or implant. This insures that the bone cement prosthesis interface has assured mechanical property characteristics at the critical location. This assists the surgeon by assuring him that operating room conditions are not as critical in that regard. The collar 20 also assists the surgeon by assuring proper placement of the prosthesis 10 relative to the opening 0 and bone F and the mechanical or anatomic axis of the bone accommodating the implanted component. Further, the bonded bone cement material is precluded from any undesired, inadvertent movement during the curing process.

USE AND OPERATION OF THE PRESENT INVENTION

In the use and operation of the invention, the surgeon will utilize the conventional techniques and procedures to prepare the opening 0 or cavity in any particular bone for prosthesis placement. The opening 0 will normally be formed to provide the compatible size and shape for the chosen collar 20. If desired, the surgeon may employ a plug such as disclosed in U.S. Pat. No. 4,302,855 to block the intramedullary canal.

After the bone cement is prepared, a prechosen volume is then inserted into the bone opening 0 and worked under pressure by the surgeon to remove any air bubbles and to force the cement into intimate contact with the bone structure. This may be done either using injection equipment or using his hands as the surgeon desires. When the surgeon is satisfied with the consistency of the bone cement and other appropriate factors or consideration involved with the use of bone cement, the preformed apparatus A of the present invention is then inserted into the cavity.

As the stem portion 14 moves into the bone cavity, it begins to displace the bone cement C and effect bone cement flow or movement in the opening 0. When the apparatus A is initially inserted, the stem 10 commences to act as a plunger for forcing flow of the dough like bone cement into the intertices of the femur as the stem 14 moves into the opening the bone cement C is displaced and is free to flow upwardly in the annular area between the stem 14 and the femur F outwardly of the opening 0. Such flow is virtually unrestricted from the opening 0 until the collar 20 becomes adjacent the opening of the bone structure. At that time, the preformed collar 20 on the implant apparatus serves to restrict the exit flow and commences to build up pressure in the bone cement C. During the last increment of movement of the stem 14 the tapered collar begins to restrict the flow of the viscous bone cement C from the opening and commences to gradually build up a back pressure on the bone cement. This, of course, is desirable as it will force the air from the bone cement or decrease the size of the voids of any entrapped air and thereby increase the mechanical strength of the cement. By adjusting the selection of the length and taper of the collar 14, and the rate of component insertion, the surgeon can control the pressure build up in the bone cement C. Continued insertion by the surgeon of the implanted prosthesis 10 will further pressurize the bone cement C in the bone opening 0 during the final increment of insertion movement and either force the escape of air or compress the air bubbles entrapped in the bone cement. In addition, the preformed collar of bone cement insures the proper concentric spacing of the prosthesis with the bone to insure that no bone to prosthesis contact occurs. Preferably, immediately before insertion is complete an operable seal is effected between the collar 14 and bone F to assure pressurization during the bone cement curing time. The collar 20 during the last increments of travel into the opening affects a fluid pressure seal with the femur F and places the viscous fluid in compression. Such compression is maintained during the curing process for affecting the enhanced suitable bond. When the prosthesis is properly positioned the bone cement is allowed to cure in the usual manner and the surgery is completed using known techniques.

The foregoing disclosure and description of the invention are illustrative and explanatory thereof, and various changes in the size, shape and materials, as well as in the details of the illustrated construction, may be made without departing from the spirit of the invention.

What is claimed is:

1. A method of preparing a prosthesis for subsequent securing within a surgically prepared opening in a patient's bone using plastic bone cement, including the steps of:
    bonding to the prosthesis a shaped layer of plastic bone cement comparable material of sufficient annular thickness to form sealing collar means for operably effecting a pressurizing seal with the anticipated size of the bone opening during the final increment of movement of the prosthesis during insertion into the surgically prepared bone opening for securing and;
    curing the layer of bone cement compatible material under controlled pressurized conditions to obtain a desired minimum level of mechanical properties of the bone cement compatible material prior to securing the prosthesis within the prepared opening.

2. The method as set forth in claim 1, wherein:
    the step of bonding includes controlling the minimum thickness of the layer of bone cement compatible material to assure a sufficient interface thickness of optimum cured bone cement compatible material for protecting the bone from direct contact with the prosthesis.

3. The method as set forth in claim 1, wherein:
    the step of bonding includes the step of shaping the layer of bone cement compatible material to restrict the escape of bone cement from the opening prior to final insertion of the prosthesis.

4. A prosthesis comprising a prosthetic element and a ring-like sealing sleeve fixedly adhered to at least a portion of the surface of said prosthetic element;
    said ring-like sleeve fixedly adhered to at least a portion of the surface of said prosthesis element and formed of a material compatible with the bone cement used for securing the prosthesis;
    said sleeve being shaped to provide a means for sealing with the bone during the final increment of insertion of the prosthesis to pressurize the bone cement during curing.

5. A prosthesis in accordance with claim 4, wherein:
    said prosthetic element is composed of metal.

6. A prosthesis for surgically implanting in a human using bone cement, including:
    a prosthesis for forming a portion of a human skeleton, said prosthesis adapted to be received in an opening of a bone prepared by a surgeon,
    means formed on said prosthesis for forming a ring-like sleeve for sealing with the bone adjacent the opening during the final increment placement of the prosthesis in the opening to pressurize the bone cement in said opening prior to curing.

7. A method of implanting a prosthesis in a surgically prepared opening of a bone using a curable plastic bone cement, including the steps:
    preparing an opening in a bone to receive a prosthesis;
    placing plastic bone cement in the opening; and
    inserting the prosthesis into the opening, said prosthesis having a ring-like collar means formed thereon;
    pressurizing the bone cement during insertion of the prosthesis by sealing the collar means on said prosthesis to the bone; and
    curing the pressurized bone cement.

* * * * *